United States Patent [19]
Hong et al.

[11] Patent Number: 5,925,551
[45] Date of Patent: Jul. 20, 1999

[54] ASPERGILLUS GENUS SHOWING RESISTANCE TO CERULENIN AND L-METHIONINE ANALOGUE AND A PROCESS FOR PREPARING MEVINOLINIC ACID THEREFROM

[75] Inventors: Chung-Il Hong, New York, N.Y.; Jung-Woo Kim, Seoul, Rep. of Korea; Kyung-Hwan Kim, Seoul, Rep. of Korea; Byoung-Tack Choi, Seoul, Rep. of Korea; Jang-Woo Park; Byoung-Kook Kim, both of Kyunggi-Do, Rep. of Korea

[73] Assignee: Chong Kun Dang Corporation, Seoul, Rep. of Korea

[21] Appl. No.: 08/961,455

[22] Filed: Oct. 30, 1997

[30] Foreign Application Priority Data

Aug. 1, 1997 [KR] Rep. of Korea ............ 97-37011
Oct. 21, 1997 [KR] Rep. of Korea ............ 97-53987

[51] Int. Cl.$^6$ .............. C12P 7/62; C12N 1/14; C12N 1/16
[52] U.S. Cl. .......... 435/135; 435/125; 435/254.3; 435/256.1; 435/913
[58] Field of Search .............. 435/256.1, 254.3, 435/913, 135, 125

[56] References Cited

U.S. PATENT DOCUMENTS 4,231,938 11/1980 Monaghan et al. ............ 435/125
5,403,728 4/1995 Jekkel et al. ............ 435/125

FOREIGN PATENT DOCUMENTS

WO 95/12661 5/1995 WIPO .

OTHER PUBLICATIONS

K. Kirimura et al., Intraspecific Protoplast Fusion of Citric Acid–Producing Strains of Aspergillus niger, J. Ferment. Technol., 64:473–479 (1986).

M.–S. Shiao and H.–S. Don, Biosynthesis of Mevinolin, A Hypocholesterolemic Fungal Metabolite, in Asperguillus terreus, Proc. Natl. Sci. Counc. B. ROC, 11:223–231 (1987).

S. Omura, The antibiotic Cerulenin, a Novel Tool for Biochemistry as an Inhibitor of Fatty Acid synthesis, Bacteriol. Rev., 40:681–697 (1976).

R.N. Moore et al., Biosynthesis of the Hypocholesterolemic Agent Mevinolin by Aspergillus terreus. Determination of the Origin of Carbon, Hydrogen, and Oxygen Atoms by $^{13}$C NMR and Mass Spectrometry, J. Am. Chem. Soc., 107:3694–3701 (1985).

H. Funabashi et al., Binding Site of Cerulenin in Fatty Acid Synthetase, J. Biochem., 105:751–755 (1989).

V.A. Vinci et al., Mutants of Lovastatin–Hyperproducing Aspergillus terreus Deficient in the Production of Sulochrin, J. Ind. Micro., 8:113–120 (1991).

A. Kawaguchi et al., Cerulenin Resistance in a Cerulenin–Producing Fungus, Arch. Biochem. Biophys. 197:30–35 (1979).

G.E. McElhaney–Feser and R.L. Cihlar, Basis of Cerulenin Resistance of two Strains of Candida albicans, Microbiology, 141:1553–1558 (1995).

M. Hosobuchi et al., Production of ML–236B, and Inhibitor of 3–Hydroxy–3–Methylglutaryl CoA Reductase, by Penicillium citrinum: Improvements of Strain and Culture conditions, Biosci. Biotech. Biochem. 57:1414–1419 (1993).

D.R. Hoffman et al., S–Adenosylmethionien and S–Adenosylhomocysteine Metabolism in Isolated Rat Liver, J. Biol. Chem., 255:1082–10827 (1980).

N. Shiomi et al., Improvement of S–Adenosylimethionine Production by Integration of the Ethionine–Resistance Gene into Chromosomes of the Yeast Saccharomyces cerevisiae, Appl Microbiol Biotechnol., 42:730–733 (1995).

M.K.Chattopadhyay et al., Threonine Analogue Resistant Mutants of Escherichia coli K–12, Biotech. Lett., 17:567–570 (1995).

M. Hiltunen and K. Soderhall, Inhibition of Polyketide Synthesis in Alternaria alternate by the Fatty Acid Synthesis Inhibitor Cerulenin, Appl. Environ. Microbiol., 58:1043–1045 (1992).

R.L. Monaghan et al., Discovery of Novel Secondary Metabolites from Fungi–is it really a random walk through a random forest?, Can. J. Bot., 73:S925–S931 (1995).

F. Kreuzaler and K. Hahlbrock, Enzymic Synthesis of an Aromatic Ring from Acetate Units, Eur. J. Biochem., 56:205–213 (1975).

J.F. Martin and L.E. McDaniel, Specific Inhibition of Candicidin Biosynthesis by the Lipogenic Inhibitor Cerulenin, Biochim. Biophys. Acta., 411;186–194 (1975).

H. Ohno et al., Inhibition of 6–Methylsalicylic Acid Synthesis by the Antibiotic Cerulenin, J. Biochem., 78:1149–1152 (1975).

S. Omura and H. Takeshima, Inhibition of the Biosynthesis of Leucomycin, a Macrolide Antibiotic, by Cerulenin, J. Biochem., 75:193–195 (1974).

T. Ohno et al., Target of Inhibition by the Anti–Lipogenic Antibiotic Cerulenin of Sterol Synthesis in Yeast, Biochem. Biophys. Res. Comm., 57:1119–1124 (1974).

Y. Yoshizawa et al., Revision of the Biosynthetic Origin of Oxygens in Mevinolin (Lovastatin), a Hypocholesterolemic Drug from Aspergillus terreus MF 4845, J. Am. Chem. Soc., 116:2693–2694 (1994).

Primary Examiner—Herbert J. Lilling
Attorney, Agent, or Firm—Knobbe, Martens, Olson & Bear, LLP

[57] ABSTRACT

The present invention relates to a novel mutant of Aspergillus terreus which shows a resistance to both cerulenin and L-methionine analogue, and a process for preparing mevinolinic acid which comprises aerobic culture of the mutant strain and recovery of mevinolinic acid. The mutant of the present invention provides a remarkably high productivity of mevinolinic acid while reducing the production of byproducts such as mevinolinic acid analogues, when compared with a wild type Aspergillus terreus isolated from soil environment in Korea, and it successfully produce mevinolinic acid by employing monosaccharides such as glucose and galactose, unlike the mother strain.

10 Claims, 1 Drawing Sheet

ASPERGILLUS GENUS SHOWING RESISTANCE TO CERULENIN AND L-METHIONINE ANALOGUE AND A PROCESS FOR PREPARING MEVINOLINIC ACID THEREFROM

BACKGROUND OF THE INVENTION

1. Field of the Invention

The present invention relates to a novel microorganism which belongs to Aspergillus genus and shows a resistance to both cerulenin and L-methionine analogue and a process for preparing mevinolinic acid therefrom, more specifically, to a novel mutant of *Aspergillus terreus* resistant to both cerulenin and L-methionine analogue, which provides a high productivity of mevinolinic acid while reducing the production of its analogues, and a process for preparing mevinolinic acid which comprises aerobic culture of the mutant strain and recovery of mevinolinic acid.

2. Description of the Prior Art

Lovastatin(which is also called as mevinolin) is a useful substance for the treatment of human hypercholesterolemia, hyperlipemia, etc., which plays a role as an inhibitor of HMG-CoA(3-hydroxy-3-methylglutaryl-Coenzyme A) reductase, one of enzymes involved in the rate-determining step of biosynthesis of cholesterol in human body. It is prepared by lactonization of mevinolinic acid which is produced by fermentation of molds or microorganisms belonging to *Aspergillus terreus*(see: Korean patent publication No. 83-2438; U.S. Pat. No. 4,231,938) and Monascus genus (see: Korean patent publication No. 83-2329). Lovastatin is also a starting material for the synthesis of Simvastatin, an inhibitor of HMG-COA reductase(see: Korean patent publication No. 85-669; U.S. Pat. No. 4,444,784).

Lovastatin is chemically represented as [1S-[1$\alpha$(R*),3$\alpha$,7$\beta$,8$\beta$(2S*,4S*),8$\alpha\beta$]]-2-methylbutanoic acid 1,2,3,7,8,8a-hexahydro-3,7-dimethyl-8-[2-(tetrahydro-4-hydroxy-6-oxo-2H-pyran-2-yl)ethyl]-1-naphthalenyl ester, and strains producing the compound also produce an acid form of lovastatin, i.e., mevinolinic acid, which is converted into lovastatin(mevinolin) as a lactone form in the course of isolation and recovery.

Mevinolinic acid produced from *Aspergillus terreus* is biosynthesized from acetate precursor via polyketide pathway in a similar manner as in the biosynthesis of fatty acid, and it has a chemical structure comprising a backbone derived from 9 acetate units and a side chain consisting of 2 acetate units(see: Moore et al., J. Am. Chem. Soc., 107:3694–3701(1985); Yoshizawa et al., J. Am. Chem. Soc., 116:2693–2694(1994)), and 2 methyl groups transferred from S-adenosyl methionine("SAM")(see: Ming-Shi Shiao and Hsiao-Sheck Pon, Proc. Natl. Sci. Counc. B. ROC, 11(3):223–231(1987)).

A triol polyketide synthase which plays a role in forming a backbone including 1 methyl group, except a side chain ($\alpha$-methylbutyrate) in the structure of mevinolinic acid derived from acetate, and its structural gene were isolated from *Aspergillus terreus*. It was revealed that its amino acid sequence and presumed active site are almost similar to those of a fatty acid synthetase(see: WO95/12661). Also, it was found that methyltransferation occurs from L-methionine through SAM after formation of polyketides consisting of 18 carbons and 4 carbons, respectively, during the biosynthesis of mevinolinic acid(see: Ming-Shi Shiao and Hsiao-Sheck Pon, Proc. Natl. Sci. Counc. B. ROC, 11(3):223–231(1987)).

On the other hand, it has been known that cerulenin blocks biosynthesis of sterol by inhibiting the action of HMG-CoA reductase(see: Ohno et al., Biochemical and Biophysical Research Communications, 57(4):1119–1124 (1974)) and inhibits the action of fatty acid synthetase by binding covalently with a cysteine residue of the enzyme which is involved in condensation step during the biosynthesis of fatty acid(see: Funabashi et al., J. Biochem., 105:751–755(1989)).

Moreover, cerulenin, an inhibitor of biosyntheses of fatty acid and sterol also inhibits polyketide biosynthesis(see: Satoshi Omura, Bacteriol. Rev., 40(3):681–697(1976)). Also, it has been found that biosyntheses of leucomycin(see: Omura et al., J. Biochem., 75:193–195(1974)), 6-methylsalicylic acid(see: Ohno et al., J. Biochem., 78:1149–1152(1975)), candicidin(see: Martin et al., Biochimica et Biophysica Acta, 411:186–194(1975)), flavanone (see: Kreuzaler, F & K. Hahlbroch, Eur. J. Biochem., 56:205–213(1975)) and alternariol(see: Hiltunen et al., Applied and Environmental Microbiology, 58(3):1043–1045(1992)), all of which pass through the pathway of polyketide biosynthesis, are inhibited by cerulenin.

Although cerulenin inhibits biosynthesis of fatty acid, *Cephalosporium caerulens*, a microorganism producing cerulenin can grow even in a medium containing a high concentration(about 100 $\mu$g/ml) of cerulenin, and it was reported that such a resistance to cerulenin results from the resistance of its fatty acid synthetase to cerulenin(see: Kawaguchi et al., Archives of Biochemistry and Biophysics, 197(1):30–35(1979)). Also, characterization of a cerulenin-resistant strain isolated from *Candida albicans* revealed that its resistance to cerulenin results from remarkable decrease of intracellular uptake of cerulenin and decrease of inhibitory action of cerulenin on fatty acid synthetase(see: Cail McElhaney-Feser and Ronald L., Cihlar, Microbiology, 141:1553–1558(1995)).

On the other hand, *Aspergillus terreus* ATCC 20541 and ATCC 20542 known as microorganisms producing mevinolinic acid, or other known mevinolinic acid producing strains(see: Korean patent publication No. 83–2438; U.S. Pat. No. 4,231,938; Menaghan et al., Can. J. Bot., 73(suppl.1):S925–S931(1995)) have shortcomings of low productivity of mevinolinic acid(for example, productivity of mevinolinic acid of *Aspergillus terreus* ATCC 20541 is 10–80 $\mu$g/ml, and that of *Aspergillus terreus* ATCC 20542 is 50–850 $\mu$g/ml) and high production of mevinolinic acid analogues. In this regard, although it has been reported that a mutant of *Aspergillus terreus*ATCC 20542 obtained by conventional mutation and screening technologies, produced mevenolinic acid in increase of 20% compared with a mother strain, while reducing the production of its analogues such as sulochrin in decrease of 83%(see: Vinci et al., Journal of Industrial Microbiology, 8:113–120(1991)), the mutant strain has proved to be less satisfactory in a sense that it still produces some analogues including triol acid highly, while providing a low productivity of mevinolinic acid. Accordingly, there are strong reasons for exploring and developing alternative means for high production of mevinolinic acid, while reducing the production of its analogues such as asterric acid, butyrolactone, citrinin, emodin, itaconic acid, geodin, sulochrin, terretonin, etc.

SUMMARY OF THE INVENTION

The present inventors have made an effort to solve the disadvantages of the known microorganisms of low productivity of mevinolinic acid and high production of its analogues, focusing on the previous reports that: biosynthesis of lovastatin occurs via polyketide pathway, an enzyme participating in the biosynthesis of lovastatin is similar to fatty acid synthetase, 2 methyl groups are transferred from L-methionine through SAM, and L-methionine analogues inhibit biosynthesis of methionine, conversion of methionine into SAM and methyltransferation from SAM(see: Chattopadhyay et al., Biotechnology Letters, 17(6):567–570 (1995); Shiomi et al., Appl. Microbiol. Biotechnol., 42:730–733(1995); Hoffman et al., The Journal of Biological Chemistry, 255(22):10822–10827(1980)).

Also, based on an idea that side reaction in biosynthetic pathway should be minimized, while maximizing the supply of precursors, to accomplish high production of a desired product, they have tried to develop novel strains assuring high production of mevinolinic acid, which utilize precursors in biosynthesis of mevinolinic acid rather than biosynthesis of fatty acid or sterol since mevinolinic acid synthase and fatty acid synthetase utilize acetate as a common precursor.

As a result, they discovered that a novel mutant strain of Aspergillus terreus has a productivity of mevinolinic acid in increase of 15-fold or more, while producing mevinolinic acid analogues in decrease of about 90% or more, when compared with a mother strain. In this regard, the mutant strain of the invention, "Aspergillus terreus CLS216-71" (deposited with the Korea Research Institute of Bioscience and Biotechnology Korean Collection for Type Cultures, #52, Oun-dong, Yusong-ku, Taejon 305–333, Republic of Korea, under Accession No. KCTC 0359BP) was obtained in accordance with the folowin rocedures: strains resistant to cerulenin, an inhibitor of biosyntheses of fatty acid, sterol, polyketide antibiotics, etc., and DL-ethionine, a L-methionine analogue, respectively, were first selected by the mutagenesis of Aspergillus terreus, and a mutant resistant to both cerulenin and L-methionine analogue was prepared by protoplast fusion of both strains.

A primary object of the invention is, therefore, to provide a novel microorganism of Aspergillus genus which shows resistance to both cerulenin and L-methionine analogue.

The other object of the invention is to provide a process for preparing mevinolinic acid employing the said microorganism.

BRIEF DESCRIPTION OF THE DRAWINGS

The above and the other objects and features of the present invention will become apparent from the following descriptions given in conjunction with the accompanying drawings, in which.

DETAILED DESCRIPTION OF THE INVENTION

Figure 1:
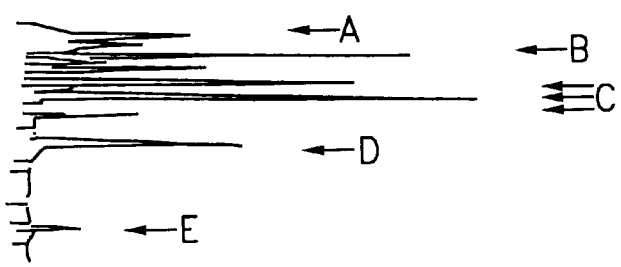
FIG. 1 is a HPLC chromatogram of acetone extract of cultured medium of a wild-type Aspergillus terreus CKL031.

The present inventors have prepared a novel microorganism which belongs to Aspergillus genus in accordance with the following procedures: they first isolated Aspergillus terreus, a strain producing mevinolinic acid from soil environment in Korea, treated the strain with mutagens, obtained a mutant resistant to cerulenin, an inhibitor of biosyntheses of fatty acid and polyketide antibiotics and a mutant resistant to the analogue of L-methionine, a substance transferring methyl group in the biosynthesis of mevinolinic acid, respectively, finally, they fused those mutants by protoplast fusion to obtain the novel Aspergillus genus of the present invention.

The wild-type mevinolinic acid producing Aspergillus terreus(hereinafter, referred to as "Aspergillus terreus CKL031") was isolated from soil, and treated with conventional mutagens known in the art, e.g., ultraviolet ray or chemicals, to select a mutant which shows an increased productivity of mevinolinic acid and a reduced productivity of its analogues(hereinafter, referred to as "Aspergillus terreus CKL043"). The selected mutant CKL043 was used as a parent strain for selection of strains showing a resistance to cerulenin and L-methionine analogue, respectively.

In order to obtain a cerulenin-resistant mutant, the parent strain Aspergillus terreus CKL043 was cultured in an agar slant medium, and the spores thus produced were harvested. Then, the spore suspension was treated with ultraviolet ray or chemicals, and cerulenin-resistant mutants were screened using a medium containing cerulenin. Among the cerulenin-resistant mutants thus isolated, a mutant showing both high inhibitory action on the growth of a test organism and high production of mevinolinic acid was selected. The mutant thus selected provided a productivity of mevinolinic acid in increase of 4.4-fold or more at 10 days after culture, when compared with a mother strain CKL031.

In addition, a L-methionine analogue-resistant mutant was also obtained in a similar manner as in the cerulenin-resistant mutant, except for using a medium containing L-methionine analogues in the course of screening. Among the L-methionine analogue-resistant mutants thus isolated, a mutant showing both high inhibitory action on the growth of a test organism and high production of mevinolinic acid was selected. In this connection, DL-ethionine, DL-norleucine, seleno methionine, α-methylmethionine or sinefungin was used as a L-methionine analogue in a concentraion of 3.5–5 mg/ml. The mutant thus selected provided a productivity of mevinolinic acid in increase of 3.8-fold or more at 10 days after culture, when compared with a mother strain CKL031.

In order to obtain a mutant resistant to both cerulenin and L-methionine analogue from the cerulenin-resistant mutant and the L-methionine analogue-resistant mutant, protoplast fusion of the two mutants was performed according to Kirimura et al's method(see: Kirimura et al., J. Ferment. Technol., 64(6):473–479(1986)). After respective preparation of protoplasts of the two mutants, the protoplasts were mixed and seeded onto a medium containing both cerulenin and L-methionine analogue. Colonies growing on the medium containing both cerulenin and L-methionine analogue were selected, cultured again on a solid minimal medium containing d-camphor, a heterodiploid-inducing substance, harvested and cultured in a liquid medium to select a mutant CLS216-7 which has a productivity of mevinolinic acid in increase of 4-fold or more and 15-fold or more, when compared with the cerulenin-resistant mutant and the mother strain CKL031, respectively.

On the other hand, when the selected mutant was appropriately diluted and seeded onto a solid medium containing benomyl, a haploid-inducing substance and containing no benomyl, respectively, each colony formed two sectors of different shape of strain on the solid medium containing benomyl(see: Kirimura et al., J. Ferment. Technol., 64(6):473–479(1986)). Accordingly, it was demonstrated that the mutant CLS216-7 of the invention resistant to both cerulenin and L-methionine analogue, has a stable productivity of mevinolinic acid which affords its successful application for industrial use.

Also, the mutant CLS216-7 selected in the present invention, showed about 90%, 25% and 28% reduction in content of mevinolinic acid analogues, when compared with the mother strain, the cerulenin-resistant mutant and the L-methionine analogue-resistant mutant, respectively. Accordingly, it has an advantage that costs can be remarkably reduced by the simplification of seperation and purification during industrial scale production of mevinolinic acid by fermentation.

The mutant strain of the invention CLS216-7 may be cultured in a medium comprising carbon source, nitrogen source, inorganic substances, anti-foaming agent, etc., at a temperature range of 25–36° C., preferably 27–30° C. under a pH condition of 5.5–7.5. In this connection, lactose, dextrin, maltose, starch, soluble starch, fructose, sucrose, xylose, glucose, galactose and glycerol may be used as a carbon source alone or in combination. For example, combination of lactose and dextrin, lactose and soluble starch, lactose and starch, or maltose and soluble starch may be used as a carbon source. Organic and inorganic nitrogen source such as corn steep liquor, dried yeast, peptone, casein, soy bean powder, ammonium sulfate, ammonium nitrate and sodium nitrate may be used as a nitrogen source alone or in combination. Inorganic substances may be varied depending on the medium, and iron, manganese, copper, calcium, boron, molybdenum and zinc are preferably employed as inorganic substances. PPG2000(polypropylene glycol 2000) and SAG™(OSi Specialties Inc., USA), polyols of silicon type may be used as anti-foaming agents. Particularly, the mutant CLS216-7, unlike the mother strain, has characteristics that inhibition of mevinolinic acid production by monosaccharides such as glucose and galactose is remarkably reduced.

Preparation of mevinolinic acid from the mutant CLS216-7 may be performed according to the known method for obtaining secondary metabolites after cultivating a strain of Aspergillus genus. Since mevinolinic acid is accumulated in an acid form in cultured medium and mycelium, it can be recovered in a form of mevinolin through extraction step after mixing them with organic solvents such as acetone in accordance with a known method in the art.

The present invention is further illustrated in the following examples, which should not be taken to limit the scope of the invention.

EXAMPLE 1

Preparation of *Aspergillus terreus* CKL043

A wild-type *Aspergillus terreus* CKL031 was isolated from soil environment in Korea by the conventional methods in the art, and cultured in an agar slant medium(complex medium, consisting of glucose 4 g/L, yeast extract 4 g/L, malt extract 10 g/L and agar 20 g/L) for 15–20 days, and the spores thus produced were resuspended in 5 ml of 20% glycerin solution, shaken sufficiently, and filtered through cheesecloth to recover spore suspension. The suspension was diluted to 10-fold with saline solution, irradiated with ultraviolet in a strength of 300 uw/cm$^2$ for 90 seconds, and seeded onto a solid complex medium or a solid minimal medium as disclosed in Table 1 below. Then, among colonies growing on the solid medium after culture at 28° C. for 10–15 days, colonies showing large growth-inhibiting zone were isolated using a test organism of *Aspergillus niger* for screening of a mutant showing a high productivity of mevinolinic acid, and seeded onto a solid complex medium.

TABLE 1

Compositions of solid complex medium and solid minimal medium

| Solid complex medium | | Solid minimal medium | |
| --- | --- | --- | --- |
| Components | Ratio | Components | Ratio |
| glucose | 4 g/L | glucose | 50 g/L |
| malt extract | 10 g/L | ammonium sulfate | 3 g/L |
| yeast extract | 4 g/L | potassium phosphate | 1 g/L |
| agar | 20 g/L | magnesium sulfate | 1 g/L |
| | | mixture of trace elements* | 1 mg/L |

*: a mixture consisting of FeSO$_4$ · 7H$_2$O 1.0 g/L, MnSO$_4$ · H$_2$O 0.5 g/L, CuSO$_4$ · 2H$_2$O 0.025 g/L, CaCO$_3$ 0.15 g/L, H$_3$BO$_3$ 0.056 g/L, (NH$_4$)$_6$MO$_7$ · 4H$_2$O 0.010 g/L, ZnSO$_4$ · 7H$_2$O 0.2 g/L and 0.5 N HCl 10 mL/L After culture at 28° C. for 20 days, 5 ml of 20% glycerin solution was added to the solid complex medium to recover spore suspensions, which were subsequently cultured in a liquid medium. That is, 30 ml of a medium for seed culture as disclosed in Table 2 below was added into a 100 ml-triangular flask, and the spore suspensions were inoculated in a ratio of 5%(v/v) against the medium for seed culture and cultured at 28° C. on a shaking incubator operating at 240 rpm for a varied time of 24–48 hours depending on growth state of the strain. Then, the cultured medium was inoculated in a 100 ml-triangular flask containing 30 ml of medium for a main culture as disclosed in Table 2 below in a ratio of 10% (v/v) against the medium for main culture, and cultured at 28° C. on a shaking incubator operating at 240 rpm for 10–15 days depending on growth state of the strain.

TABLE 2

Compositions of media employed for seed culture and main culture

| Medium for seed culture | | Medium for main culture | |
| --- | --- | --- | --- |
| Components | Ratio | Components | Ratio |
| soluble starch | 10 g/L | soluble starch | 200 g/L |
| glucose | 10 g/L | soy bean powder | 40 g/L |
| starch soaking solution | 4 g/L | yeast extract | 1 g/L |
| soy bean powder | 10 g/L | phosphoric acid | 0.05 ml/L |
| bean oil | 2.5 g/L | PPG 2000 | 5 ml/L |
| mixture of trace elements* | 10 ml/L | mixture of trace elements* | 5 ml/L |

*: a mixture consisting of FeSO$_4$ · 7H$_2$O 1.0 g/L, MnSO$_4$ · H$_2$O 0.5 g/L, CuSO$_4$ · 2H$_2$O 0.025 g/L, CaCO$_3$ 0.15 g/L, H$_3$BO$_3$ 0.056 g/L, (NH$_4$)$_6$MO$_7$ · 4H$_2$O 0.010 g/L, ZnSO$_4$ · 7H$_2$O 0.2 g/L and 0.5 N HCl 10 mL/L To 3 ml of the medium containing the strain was added 3 ml of acetone, and stirred at 28° C. for 30 minutes on a shaking incubator operating at 240 rpm. The extract thus obtained was centrifuged, and aliquot of the supernatant was subjected to HPLC under a condition for analysis of mevinolinic acid and its analogues as followings.

Condition for HPLC analysis:

Column: Partisil 50DS-3(3 um, 4.6×250 cm, Whatman, USA)

Mobile phase: acetonitrile:0.1% H$_3$PO$_4$ in D.W.=60:40

Temperature: room temperature

Flow rate of mobile phase: 1.0 ml/min

Detection: 235 nm

As a result, a mutant strain CKL043 which has a productivity of mevinolinic acid in increase of about 4.4-fold and shows production of its analogues in decrease of 35% when compared with a mother strain *Aspergillus terreus* CKL031, was selected. The mutant was used for selection of strains resistant to cerulenin and DL-ethionine, respectively, as described in the following examples.

EXAMPLE 2

Preparation of a Mutant Resistant to Cerulenin

*Aspergillus terreus* CKL043, a parent strain prepared in Example 1 was cultured, and spore suspension was obtained in an analogous manner as in Example 1. The suspension thus obtained was washed with saline solution, irradiated with ultraviolet of 300 uw/cm$^2$ for 90 seconds for mutagenesis, seeded onto a solid minimal medium containing 100 ug/ml(0.45 mM) of cerulenin, and cultured for 8–12 days at 28° C. to isolate viable mutant strains.

Among the cerulenin-resistant mutants thus isolated, mutants showing larger growth-inhibiting zone against *Aspergillus niger* than the parent strain were first selected. The mutants thus obtained were cultured in liquid media in the same manner as described in Example 1 to select 5 mutants showing a high productivity of mevinolinic acid.

And then, the selected mutants showing both resistance to cerulenin and high productivity of mevinolinic acid were subcultured on solid minimal media containing cerulenin in gradually increasing concentrations(i.e., 110, 120, 130, 140 and 150 mg of cerulenin per ml) to select a mutant showing the highest resistance(hereinafter, referred to as "*Aspergillus terreus* CLC063"). The mutant CLC063 has 4.4-fold and 2.1-fold of productivity of mevinolinic acid, when compared with the mother strain CKL031 and the parent strain CKL043, respectively, and was employed for protoplast fusion in the following Example 4.

The cerulenin-resistant mutant thus selected has characteristics that: growth decreases remarkably during solid and liquid culture compared with the mother strain and the parent strain, and node of hypha is short during observation through microscope.

EXAMPLE 3

Preparation of a Mutant Strain Resistant to L-methionine Analogue

Mutants resistant to L-methionine analogue were isolated in the same manner as in Example 2 except that spore suspension of ultraviolet-treated parent strain, *Aspergillus terreus* CKL043 was seeded onto a solid minimal medium containing 3 g/ml of DL-ethionine.

Among the DL-ethionine-resistant mutants thus isolated, mutants showing larger growth-inhibiting zone against *Aspergillus niger* than the parent strain were primarily selected, and cultured in liquid media in the same manner as in Example 1 to select 6 mutants showing a high productivity of mevinolinic acid.

And then, the selected mutants showing both resistance to DL-ethionine and high productivity of mevinolinic acid were subcultured on solid minimal media containing DL-ethionine in gradually increasing concentrations(i.e., 3.5, 4.0, 4.5 and 5 mg of DL-ethionine per ml) to select a mutant showing the highest resistance(hereinafter, referred to as "*Aspergillus terreus* CLE082"). The mutant CLE082 has a productivity of mevinolinic acid of 2.8 g/L, i.e., 3.8-fold and 1.8-fold of productivity, when compared with the mother strain CKL031 and the parent strain CKL043, respectively, and was also employed for protoplast fusion in the following Example 4, accompanying with the cerulenin-resistant mutant CLC063 obtained in Example 2.

On the other hand, when 1.0 g/L of L-methionine was added to a liquid medium, the DL-ethionine-resistant CLE082 mutant, the mother strain CKL031 and the parent strain CKL043 produced mevinolinic acid in increase of about 10%, in decrease of 20% and in decrease of 15%, respectively, when compared with an experiment without addition of L-methionine.

EXAMPLE 4

Preparation of *Aspergillus terreus* CLS216-7 Showing a Resistance to Both Cerulenin and DL-Ethionine (1) Preparation of protoplast The cerulenin-resistant mutant CLC063 and the DL-ethionine-resistant mutant CLE082 obtained in Examples 2 and 3, were resuspended in respective 500 ml-Sakaguchi flasks containing 50 ml of a liquid limited medium in a spore concentration of 2×10$^6$/ml, and cultured at 28° C. on a shaking incubator operating at 230 rpm under an aerobic condition for 24 hours.

The mycelia thus cultured were filtered through glass filters having a pore size of 20–30 um(Shibata Scientific Technology, Ltd., JAPAN), washed twice with 0.05M phosphate buffer(pH 6.0) containing 0.7M KCl, and harvested. Then, the mycelia thus obtained were transferred onto Whatman No.1 filter paper(Whatman, USA), and washed with the same buffer again. 250 mg(wet weight) of the mycelia thus washed was resuspended in 10 ml of mixed solution of cell wall-lytic enzymes(Novozym 234, Novo Enzyme Products Ltd., Denmark) and cellulase CP(John and E. sturge Ltd., United Kingdom), and cultured at 30° C. on a shaking incubator operating at 60 rpm for 2 hours in 50 ml-Erlenmeyer flask. The mixtures thus obtained were filtered through glass filters having a pore size of 20–30 um to remove mycelial debris, and number of protoplasts in the filtered solutions was counted under a microscope using hemacytometer.

In order to purify protoplasts, 8 ml of the filtered solution was added to 1 ml of 1.4M sorbitol solution, and centrifuged at 800×g for 15 minutes to recover protoplasts in sorbitol layer. Then, the protoplasts thus obtained was added with the buffer, centrifuged, and washed.

(2) Protoplast fusion

The protoplasts of the cerulenin-resistant mutant CLC063 and the DL-ethionine-resistant mutant CLE082 were mixed in several different ratios near 2×10$^7$:2×10$^7$, and polyethyleneglycol(PEG) solution(0.05M glycine-NaOH buffer(pH 7.5) containing 30%(w/v) PEG 6000, 0.01M CaCl$_2$ and 0.5M KCl) was added to the protoplast mixtures in a final volume of 5 ml. Then, after incubation at 30° C. for 10 minutes, the mixtures were diluted slowly with 0.05M phosphate buffer(pH 6.0) containing 0.7M KCl, centrifuged at 800×g for 15 minutes, and resuspended in the same buffer. The resuspended protoplasts were diluted and seeded onto a solid minimal medium containing 0.7M KCl("SMM") and a solid minimal medium containing 0.7M KCl, 150 ug/ml cerulenin and 5 mg/ml DL-ethionine("SMMCE"), respectively. Then, SMM and SMMCE which further contain 0.5% agar and pre-heated at a temperature of 40° C., were poured onto the seeded solid media in a thickness of 0.3 cm, respectively, and cultured at 30° C. for 5 days to regenerate protoplasts.

As a result, it was found that regeneration frequencies of the mother strain, the cerulenin-resistant mutant and the L-methionine analogue-resistant mutant are 12%, 7% and 11%, respectively. Also, fusion frequency of protoplast represented as a ratio of number of colonies formed on SMMCE and SMM, respectively, was 5.8%. On the other hand, reversion frequencies from the cerulenin- and DL-ethionine-resistant strain to the parent strains, i.e., CLC063 and CLE082, were negligible values of $2.5 \times 10^{-6}$ and $5.8 \times 10^{-6}$, respectively.

According to the methods illustrated as aboves, several colonies growing on solid minimal media containing both cerulenin and DL-ethionine were selected and cultured again on solid minimal media containing 0.5 g/L of d-camphor which is a heterodiploid-inducing substance, for each 10 days through 3 generations, finally to select a mutant CLS216-7 which shows a resistance to both cerulenin and DL-ethionine and has the highest productivity of mevinolinic acid. Also, it was confirmed that the mutant CLS216-7 can maintain morphological characteristics, resistance to both cerulenin and DL-ethionine and high productivity of mevinolinic acid constantly on a solid minimal medium containing 2 g/L of yeast extract for 10 generations.

The mutant microorganism of the present invention, *Aspergillus terreus* CLS216-7 was deposited with the Korean Collection for Type Cultures(KCTC) affiliated to Korea Research Institute of Bioscience and Biotechnology (KRIBB), an international depositary authority as deposition No. KCTC 0359BP on Jul. 29, 1997.

EXAMPLE 5

Mycological Characteristics of the Protoplast-Fused Mutant CLS216-7 and the Wild Type CKL031

After culturing the protoplast-fused mutant of the invention CLS216-7 and the wild type CKL031, their morphological, cultural and physiological characteristics were examined, compared and summarized in Table 3 below. Comparison of the contents of fatty acid and sterol were made between the mutant CLS216-7 showing a high productivity of mevinolinic acid and the mother strain CKL031, grounded on the facts that cerulenin, an inhibitor of fatty acid biosynthesis was used for screening of resistant strains in the present invention, and biosyntheses of fatty acid and sterol compete with that of mevinolinic acid for utilization of Acetyl-CoA. In this connection, analyses of fatty acid and sterol were carried out according to Hosobuchi et al.'s method(see: Hosobuchi et al., Biosci. Biotech. Biochem., 57(9):1414–1419 (1993)).

TABLE 3

Characteristics of the wild type strain and the protoplast-fused mutant

| Characteristics | The mother strain CKL031 | The mutant CLS216-7 |
|---|---|---|
| color of colony | pale yellow | pale gray |
| shape of colony | even surface, round and spreading circumference, thickness: 0.2–0.3 mm, diameter: 5–10 mm | wrinkled surface and circumference, small size, thickness: 0.3-0.4 mm, diameter: 3–5 mm |
| shape and size of spore | round ellipse (1.5–2.5 um) | round ellipse (1.5–2.5 um) |
| sporulation (under the present experimental condition of fermentation) | $2.8 \times 10^8$/ml C.F.U. | $3.5 \times 10^7$/ml C.F.U. |
| growth type | filamentous, pellet type | pellet type |
| proliferation rate in solid and liquid meida | rapid | slow |

TABLE 3-continued

Characteristics of the wild type strain and the protoplast-fused mutant

| Characteristics | The mother strain CKL031 | The mutant CLS216-7 |
|---|---|---|
| color of cultured medium | yellowish brown | reddish brown |
| minimal inhibitory concentration of cerulenin | ≦50 ug/ml | ≦150 ug/ml |
| minimal inhibitory concentration of DL-ethionine | ≦1.0 ug/ml | ≦4.5 ug/ml |
| concentration of oleic acid (ug/mg dry cell) | 2.3 | 2.1 |
| concentration of palmitic acid (ug/mg dry cell) | 0.31 | 0.32 |
| concentration of ergosterol (ug/mg dry cell) | 2.42 | 0.40 |
| temperature for optimal growth | 25–36° C. | 25–36° C. |
| optimum pH | 5.0–7.0 | 5.5–7.5 |
| productivity of mevinolinic acid during use of glucose* | inhibited remarkably | inhibited weakly |
| content of derivatives | 68% | 5% |
| productivity of mevinolinic acid | 0.7 g/L | 12.3 g/L |

*: See Table 4.

As can be seen in Table 3 above, it was revealed that he mutant CLS216-7 has remarkably reduced sporulation, ontent of ergosterol decreased to ⅙, and minimal inhibitory concentrations of cerulenin and DL-ethionine in increase of 3-fold and 4.5-fold, respectively, when compared with wild type CKL031. Also, it was found that rate and level of growth of the mutant CLS216-7 were remarkably reduced during liquid culture compared with the mother strain, that is, the mutant CLS216-7 has a specific growth rate of 0.31 and a dry cell weight of 5.6 g/L at 48 hours after culture while the mother strain(CKL031) has those of 0.40 and 7.2 g/L at 24 hours after culture.

Figure 2:
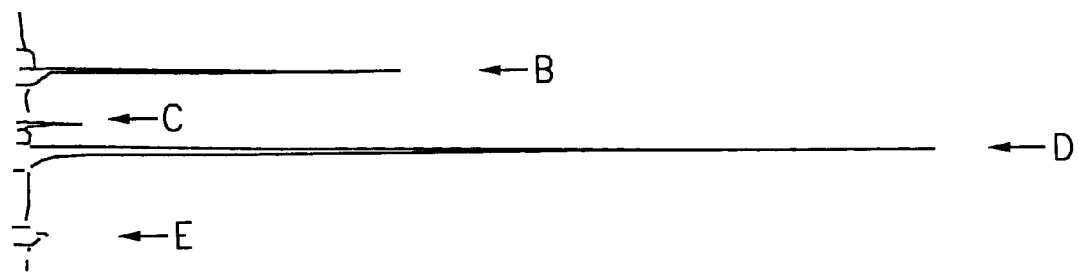
FIG. 2 is a HPLC chromatogram of acetone extract of cultured medium of a mutant strain of the invention, Aspergillus terreus CLS216-7.

On the other hand, cultured media of the wild type CKL031 and the protoplast-fused mutant CLS216-7 were extracted with acetone, and subjected to HPLC under the same condition as in Example 1(see: FIGS. 1 and 2). In FIGS. 1 and 2, A, B, C, D and E represent organic acid, acetone, analogue, mevinolinic acid and mevinolin, respectively. As shown in FIGS. 1 and 2, amount of analogues accumulated in the cultured medium of the mutant CLS216-7 which shows a resistance to both cerulenin and DL-ethionine, decreased by the percentage of 90% or more, when compared with the wild type CKL031.

Together with the remarkable reduction of mevinolinic acid analogues production, mevinolinic acid was produced in increase of about 17-fold or more(see: Table 3). Thus, it was clearly demonstrated that the mutant CLS216-7 is a well-screened microorganism in terms of mevinolinic acid production by fermentation on an industrial scale.

EXAMPLE 6

Studies on the Relationships Between Carbon Source and Mevinolinic Acid Productivity After the mother strain CKL031 and the mutant CLS216-7 were cultured for 13 days analogously as in Example 1 except that carbon source used in a medium for main culture was changed as disclosed in Table 4 below, productivity of mevinolinic acid was examined and summarized in Table 4 below.

TABLE 4

Productivity of mevinolinic acid depending on the kind of carbon source

| Carbon source | The mother strain CKL031 | | The mutant CLS216-7 | |
|---|---|---|---|---|
| | Productivity of mevinolinic acid (g/L) | Relative productivity (%) | Productivity of mevinolinic acid (g/L) | Relative productivity (%) |
| lactose | 0.690 | 100 | 12.545 | 100 |
| dextrin | 0.775 | 112 | 12.250 | 98 |
| maltose | 0.735 | 107 | 12.050 | 96 |
| soluble starch | 0.685 | 99 | 12.065 | 96 |
| fructose | 0.740 | 107 | 11.450 | 91 |
| sucrose | 0.520 | 75 | 11.202 | 89 |
| xylose | 0.820 | 119 | 11.152 | 89 |
| glucose | 0.172 | 25 | 10.754 | 86 |
| galactose | 0.180 | 26 | 10.305 | 82 |
| glycerol | 0.845 | 122 | 9.060 | 72 |

As can be seen in Table 4 above, it was revealed that the mutant CLS216-7 successfully produced mevinolinic acid by the dissimilation of monosaccarides and polysaccarides as well, while the mother strain CKL031 provides a limited productivity of mevinolinic acid when monosaccharides such as glucose and galactose were employed as carbon source.

As clearly illustrated and demonstrated as aboves, the mutant CLS216-7 of the present invention which shows a resistance to both cerulenin and L-methionine analogue, provides a remarkably high productivity of mevinolinic acid while reducing the production of byproducts such as mevinolinic acid analogues, when compared with the mother strain, *Aspergillus terreus* CKL031 and the parent strain CKL043, and it successfully produce mevinolinic acid by employing monosaccharides such as glucose and galactose, unlike the mother strain.

What is claimed is:

1. *Aspergillus terreus* CLS216-7 deposited as KCTC 0359BP.

2. A process for preparing mevinolinic acid, which comprises the steps of cultivating the *Aspergillus terreus* CLS216-7 deposited as KCTC 0359BP of claim 1 in a medium under an aerobic condition and recovering mevinolinic acid from the cultured medium.

3. The process for preparing mevinolinic acid of claim 2, wherein the medium for cultivation comprises a carbon source, a nitrogen source, an inorganic substances, and an anti-foaming agent, and the aerobic condition is set at a temperature of 25–36° C. and a pH of 5.5–7.5.

4. The process for preparing mevinolinic acid of claim 3, wherein the carbon source is one or more saccharides selected from the group consisting of lactose, dextrin, maltose, soluble starch, starch, fructose, sucrose, xylose, glucose, galactose and glycerol.

5. An *Aspergillus terreus* strain exhibiting high productivity of mevinolinic acid and resistance to both cerulenin and L-methionine analogue, which *Aspergillus terreus* strain is obtained by a method comprising the steps of:

isolating native *Aspergillus terreus* from soil;

exposing the native *Aspergillus terreus* to mutagens to produce mutants;

screening from the mutants a mutant exhibiting an increased productivity of mevinolinic acid exclusively;

culturing the screened mutant in an agar slant medium to produce spores;

exposing the spores to mutagens to produce mutants;

screening from the mutants a cerulenin-resistant mutant and a L-methionine analogue-resistant mutant by using a medium containing cerulenin and a medium containing L-methionine analogues, respectively;

selecting from the cerulenin-resistant mutant a mutant A which has higher inhibitory action on the growth of *Aspergillus niger* than does the native *Aspergillus terreus*, and which exhibits productivity of mevinolinic acid 4.4-times or higher that of the native *Aspergillus terreus* when measured at 10 days after culture;

selecting from the L-methionine analogue-resistant mutant a mutant B which has higher inhibitory action on the growth of *Aspergillus niger* than does the native *Aspergillus terreus*, and which exhibits productivity of mevinolinic acid 3.8-times or higher that of the native *Aspergillus terreus* when measured at 10 days after culture; and subjecting the mutant A and the mutant B to protoplast fusion to produce a target mutant exhibiting a resistance to both cerulenin and L-methionine analogue.

6. An *Aspergillus terreus* strain according to claim 5, wherein the L-methionine analogue is DL-ethionine, DL-norleucine, seleno methionine, α-methylmethionine, or sinefungin.

7. An *Aspergillus terreus* strain according to claim 5, whose production of mevinolinic acid is not inhibited by monosaccharides when fermented using glucose or galactose as a carbon source.

8. A process for producing mevinolinic acid, which comprises the steps of cultivating the *Aspergillus terreus* of claim 5 in a medium under an aerobic condition and recovering mevinolinic acid from the cultured medium.

9. A process for producing mevinolinic acid of claim 8, wherein the medium for cultivation comprises a carbon source, a nitrogen source, an inorganic substances, and an anti-foaming agent, and the aerobic condition is set at a temperature of 25–36° C. and a pH of 5.5–7.5.

10. A process for producing mevinolinic acid of claim 9, wherein the carbon source is one or more saccharides selected from the group consisting of lactose, dextrin, maltose, soluble starch, starch, fructose, sucrose, xylose, glucose, galactose and glycerol.

* * * * *